(12) United States Patent
Iyer et al.

(10) Patent No.: US 12,396,984 B2
(45) Date of Patent: Aug. 26, 2025

(54) MANAGING MICROBIAL DYSBIOSIS WITH TEMOCILLIN

(71) Applicant: Entasis Therapeutics, Inc., Waltham, MA (US)

(72) Inventors: Ramkumar Iyer, Arlington, MA (US); Adam Shapiro, Wellesley, MA (US); Samir Moussa, Framingham, MA (US)

(73) Assignee: Entasis Therapeutics, Inc., Waltham, MA (US)

( * ) Notice: Subject to any disclaimer, the term of this patent is extended or adjusted under 35 U.S.C. 154(b) by 681 days.

(21) Appl. No.: 17/788,146

(22) PCT Filed: Dec. 22, 2020

(86) PCT No.: PCT/US2020/066656
§ 371 (c)(1),
(2) Date: Jun. 22, 2022

(87) PCT Pub. No.: WO2021/133821
PCT Pub. Date: Jul. 1, 2021

(65) Prior Publication Data
US 2023/0068309 A1  Mar. 2, 2023

Related U.S. Application Data

(60) Provisional application No. 62/958,979, filed on Jan. 9, 2020, provisional application No. 62/952,874, filed on Dec. 23, 2019.

(51) Int. Cl.
*A61K 31/431* (2006.01)
*A61K 9/00* (2006.01)
*A61P 1/00* (2006.01)

(52) U.S. Cl.
CPC .......... *A61K 31/431* (2013.01); *A61K 9/0053* (2013.01); *A61P 1/00* (2018.01)

(58) Field of Classification Search
CPC ....... A61K 31/431; A61K 9/0053; A61P 1/00; A61P 31/04
See application file for complete search history.

(56) References Cited

U.S. PATENT DOCUMENTS

2009/0149453 A1   6/2009   Sayada

FOREIGN PATENT DOCUMENTS

| EP | 2799063 A1 | 11/2014 |
| WO | 2014/009744 A1 | 1/2014 |
| WO | 2014/116973 A1 | 7/2014 |

(Continued)

OTHER PUBLICATIONS

Seo et al., Susceptibility of *Escherichia coli* from community-acquired urinary tract infection to fosfomycin, nitrofurantoin, and temocillin in Korea. J Korean Med Sci. Aug. 2014;29(8):1178-81.

(Continued)

*Primary Examiner* — Savitha M Rao
(74) *Attorney, Agent, or Firm* — McCarter & English, LLP; Michael J. DeGrazia

(57) ABSTRACT

Provided herein are methods of using temocillin to control microbial dysbiosis arising from, in certain instances, enterobacteriacea overgrowth such as overgrowth from adherent invasive *E. coli* (AIEC). Methods of using temocillin to treat intestinal disorders and symptoms of such caused by microbial dysbiosis, as well as other disorders are contemplated herein.

16 Claims, 2 Drawing Sheets

(56) References Cited

FOREIGN PATENT DOCUMENTS

WO   2015/047941 A2   4/2015
WO   2019/178652 A1   9/2019

OTHER PUBLICATIONS

Balakrishnan et al., Temocillin: is this the right momentum for its global use? Future Microbiol. Jan. 2019;14:81-83.
Brown et al., Activity of Species-specific Antibiotics Against Crohn's Disease-Associated Adherent-invasive *Escherichia coli*. Inflamm Bowel Dis. Oct. 2015;21(10):2372-82.
Dogan et al., Multidrug resistance is common in *Escherichia coli* associated with ileal Crohn's disease. Inflamm Bowel Dis. Jan. 2013;19(1):141-50.
International Search Report and Written Opinion for Application No. PCT/US2020/066656, dated Mar. 29, 2021, 11 pages.

MANAGING MICROBIAL DYSBIOSIS WITH TEMOCILLIN

RELATED APPLICATIONS

This application is a 35 U.S.C. § 371 national stage filing of International Application No. PCT/US2020/066656, filed on Dec. 22, 2020, which in turn claims the benefit of priority to U.S. Provisional Application No. 62/952,874, filed Dec. 23, 2019, and U.S. Provisional Application No. 62/958,979, filed Jan. 9, 2020. The entire contents of each of the foregoing applications are incorporated herein by reference.

BACKGROUND

The human gastrointestinal (GI) tract harbors a complex and dynamic population of more than 100 trillion microorganisms. The collection of bacteria, arcaea, and eukarya colonizing the GI tract are known as the gut microbiota. The gut microbiota establish an intricate and mutually beneficial relationship to the host, i.e., human carrier, and offer many benefits through multiple physiological functions such as strengthening gut integrity, shaping the intestinal epithelium, harvesting energy, protecting against pathogens, and regulating host immunity. With the advent of modern technology, the implication of gut microbiota in a variety of intestinal and extra-intestinal conditions has become readily apparent. See e.g., Schroeder et al., Nat. Med. 22, 1079-1089 and Chang et al., Best Pract. Res. Clin. Gastroenterol. 30, 3-15.

Microbial dysbiosis (also referred to as dysbacteriosis) is a term that refers to the perturbation or imbalance of the normal microbiome content in the GI tract. This imbalance could be due to the gain or loss of one or more microbes with functions detrimental to the host or to the loss of one or more microbes with beneficial functions to the host. Either way, if left untreated, dysbiosis can contribute to a plethora of diseases states ranging from intestinal disorders (e.g., irritable bowel syndrome, Crohn's disease, traveler's diarrhea, colitis, ulcerative colitis, and diverticulitis) to neurodevelopmental disorders. See e.g., Guinane et. al., 2013, Therap Adv Gastroenterol. 6, 295-308.

In patients with intestinal disorders arising from microbial dysbiosis, higher populations of proteobacteria, such as Enterobacteriaceae have been observed. See e.g., Zeng et al., Mucosal Immunol. 2017 January; 10(1): 18-26 and Serino J Mol Biol. 2018 Mar. 2; 430(5):581-590. In particular, recent evidence suggest that perturbation of the microbial community favors the emergence of adherent-invasive *E. coli* (AIEC) which can increase incidence and severity of gut inflammation in the context of Crohn's disease and ulcerative colitis (see BioMed Research International, Vol. 2014, Article ID 567929, 16 pages), as well as play a role in colorectal cancer and intestinal disease in animals. See e.g., Rahmouni et al., Gut Pathogens 2018, 10:23. Two AIEC phylotypes (B2 and D) have been described as being more prevalent in IBD patients (see PLoS One, 2019, 14(4): e0216165 and Gut, 2007, 56:669-675).

AIECs affect host cell processes such as protein synthesis, signal transduction, cell division, ion secretion, transcription, cytoskeletal function, and mitochondrial function. They are particularly difficult to treat and able to adhere to the intestinal mucosa by binding to carcinoembryonic antigen-related cell adhesion molecules 6 (CEACAM6), invade intestinal epithelial cells by using host cell actin microfilaments and microtubules, replicate intracellularly, translocate across the human intestinal barrier, and move into deeper tissues. AIECs are also able to survive within macrophages, stimulate TNF-α production, and promote a granulomatous inflammatory response.

Due to their overabundance during microbial dysbiosis, their invasiveness and lack of sensitivity to various antibiotic treatments (see Dogan et al., Inflamm Bowel Dis. 2013 January; 19(1):141-50., and their downstream implications associated with intestinal and other disorders, there is a need to control AIEC overgrowth.

SUMMARY

It has now been found that temocillin is an effective modulator of adherent invasive *E. coli* (AIEC) overgrowth and, in certain instances, performs better than the current standard of care ciprofloxacin. See e.g., FIG. 1, which shows that temocillin was effective at lowering the AIEC burden in the murine GI tract and Table 1, which provides data showing lower MIC values for temocillin ($MIC_{50}$=4 or 8 μg/mL) than ciprofloxacin ($MIC_{50}$>8 μg/mL) against AIEC strains in vitro.

In another aspect, temocillin was found to have little or no effect on the normal GI flora e.g., it was determined to be microbiome sparing for at least firmicutes, actinobacteria and bacteroidetes. This is in contrast to ciprofloxacin, rifaximin, and metronidazole, each of which had broad potent antibacterial activities against firmicutes, actinobacteria and bacteroidetes. See e.g., Table 2. This is another added benefit of temocillin treatment in that there is little concern for a lack of restoration of normal healthy flora.

In another aspect, temocillin was found to be more effective at reducing the likelihood AIEC overgrowth recurrence post-treatment. See e.g., FIG. 1 where AIEC bacterial growth remained low post for at least 7 days after treatment with temocillin. Ciprofloxacin, however, showed a rebound effect. See e.g., FIG. 1.

Provided herein, therefore, are uses of temocillin, or a pharmaceutically acceptable salt thereof, for treating microbial dysbiosis.

Also provided herein are uses of temocillin, or a pharmaceutically acceptable salt thereof, for treating an intestinal disorder in a subject who is experiencing microbial dysbiosis.

Also provided are methods of modulating enterobacterial overgrowth (e.g., AIEC overgrowth) in a subject who is experiencing microbial dysbiosis or an intestinal disorder, or both.

Also provided herein are methods of treating one or more symptoms associated with microbial dysbiosis.

Further provided herein are methods of treating one or more symptoms of a disorder caused by microbial dysbiosis.

In one aspect, the aforementioned microbial dysbiosis is caused by enterobacterial overgrowth (e.g., AIEC overgrowth). Other uses of temocillin and further aspects are described in detail below.

DETAILED DESCRIPTION

A. Definitions

Figure 1:
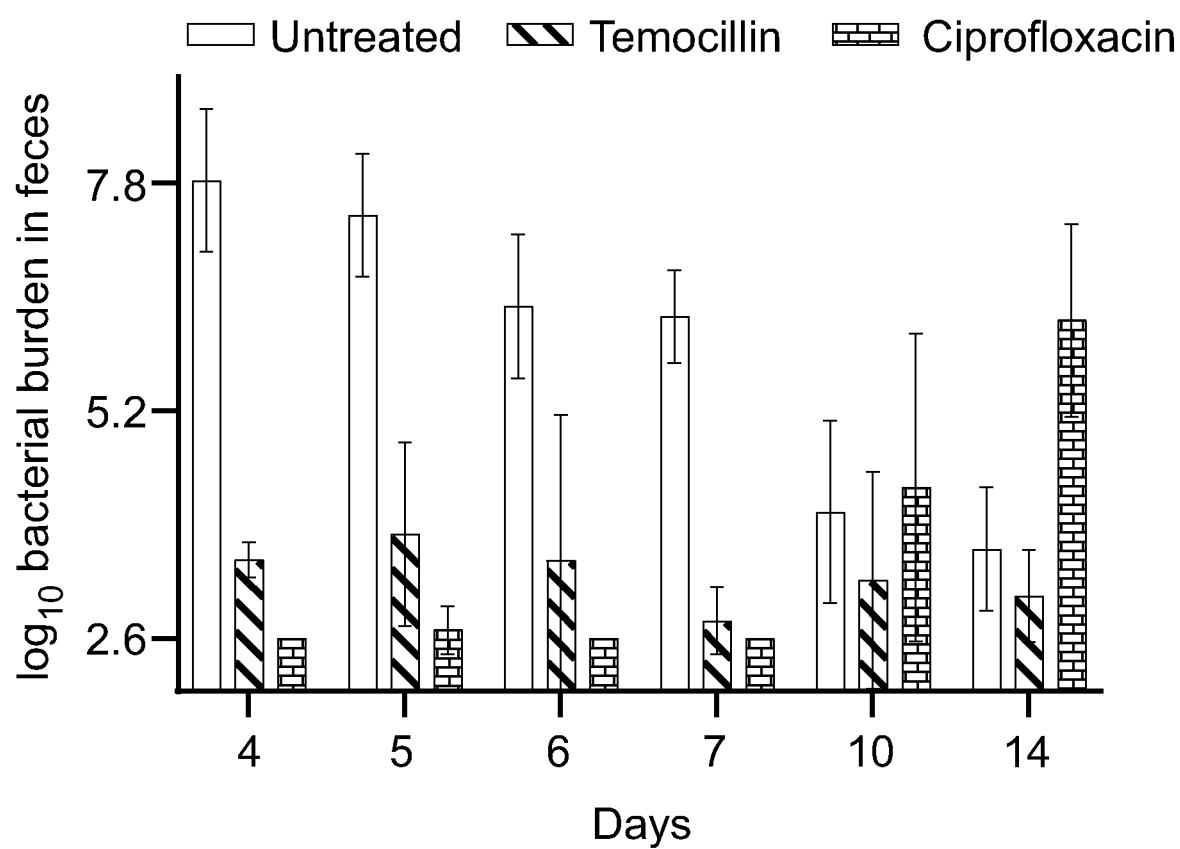
FIG. 1 depicts $\log_{10}$ bacterial burden in feces vs. days obtained from the GI AIEC Decolonization Murine Model Study of temocillin and ciprofloxacin.

As used herein, temocillin refers to the compound having the formula:

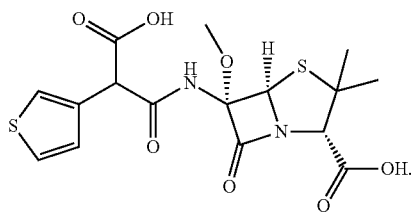 [SMILES: CO[C@@]1(NC(=O)C(C(=O)O)c2ccsc2)C(=O)N2[C@@H](C(=O)O)C(C)(C)S[C@@H]21]

Unless otherwise specified, temocillin includes the stereoisomer depicted above as well as all other possible stereoisomers and mixtures of stereoisomers. In one aspect, however, the uses described herein refer to the depicted 2S,5R,6S stereoisomer with a stereochemical enrichment or a molar excess of at least 60%, at least 65%, at least 70%, at least 80%, at least 85%, at least 90%, at least 95%, at least 97%, at least 98%, or at least 99%.

Enterobacteriaceae include, but are not limited to, *Escherichia coli* (*E. coli*), *Klebsiella, Salmonella, Shigella* and *Yersinia pestis*.

As used herein, AIEC refers to adherent invasive *E. coli*. In one aspect, AIECs can adhere to and invade cultured intestinal epithelial cells, survive and multiply within macrophages without expressing virulence factors or genes associated with diarrheagenic *E. coli* pathotypes and uropathogenic *E. coli* (UPEC). In one aspect, the characteristics of AIEC include, but are not limited to, (i) the ability to adhere to and invade intestinal epithelial cells, (ii) the ability to survive and replicate expansively within macrophages without triggering host cell death, (iii) elicit significantly elevated expression of TNF-alpha and cytokines, (iv) the lack of traditional virulence/invasion related Type III machinery known invasive determinants. See e.g., J Crohns Colitis. 2015 May; 9(5):410-20; Lab Invest. 2012 March; 92(3):411-9; and Lab Invest. 2012 March; 92(3):411-9. Characterization of AIEC can be accomplished following routine procedures known to a person of ordinary skill in the art or the procedures (e.g., the adhesion assay, the invasion assay, and the virulence genotyping assay) described in Rehmouni et al., Gut Pathogens, 2018, 10:23.

"Intestinal disorders" refers to conditions or diseases that occur in or affect the intestine. Intestinal disorders include, but are not limited to, irritable bowel syndrome (IBS) (e.g., diarrhea-associated irritable bowel syndrome (d-IBS), irritable bowel syndrome with constipation (c-IBS), alternating constipating and diarrhea irritable bowel syndrome), Crohn's disease, traveler's diarrhea, colitis, ulcerative colitis, and diverticulitis.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome. In one aspect, treatment may also be continued after symptoms have resolved, for example to delay their recurrence. "Treating" or "treatment" also refers to inhibiting and/or delaying rebound of the infection or symptoms of the infection.

As used herein, the term "modulate" means reduce, inhibit, control, or ameliorate, or sustain.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. In one aspect, however, the temocillin described in the present methods is administered in an "effective amount" or "therapeutically effective amount." This refers to an amount of temocillin that will elicit a biological or medical response of a subject e.g., a dosage of between 0.01-100 mg/kg body weight/day.

In certain aspects, the temocillin described in the present methods may be administered orally, topically, rectally, nasally, buccally, or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the temocillin described in the present methods is administered orally or rectally. In one aspect, the temocillin described in the present methods is administered orally.

The temocillin described in the present methods can be formulated so as to provide quick, sustained or delayed release of temocillin after administration to the patient by employing procedures known in the art. In one aspect, the temocillin described in the present methods is formulated as an oral delayed release composition.

Salts of temocillin described herein refer to non-toxic "pharmaceutically acceptable salts." Pharmaceutically acceptable salt forms include pharmaceutically acceptable acidic/anionic or basic/cationic salts. Suitable pharmaceutically acceptable acid addition salts include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Suitable pharmaceutically acceptable basic salts include e.g., ammonium salts, alkali metal salts (such as sodium and potassium salts) and alkaline earth metal salts (such as magnesium and calcium salts). In one aspect, the pharmaceutically acceptable salt is a sodium salt.

The term "overgrowth" when referring to increases in abundance of one or more bacteria that is beyond what is expected in otherwise healthy humans that consume a typical Western diet.

B. Uses

In a first embodiment, provided herein is a method of modulating (e.g., reducing) microbial dysbiosis in a subject in need thereof, comprising administering to the subject an effective amount of temocillin, or a pharmaceutically acceptable salt thereof. In one aspect, the microbial dysbiosis of the first embodiment is caused by enterobacterial overgrowth, e.g., AIEC overgrowth.

In a second embodiment, provided herein is a method of treating an intestinal disorder in a subject experiencing microbial dysbiosis, comprising administering to the subject an effective amount of temocillin, or a pharmaceutically acceptable salt thereof. In one aspect, the microbial dysbiosis of the second embodiment is caused by enterobacterial overgrowth, e.g., AIEC overgrowth.

In a third embodiment, provided herein is a method of reducing one or more of inflammation, diarrhea, fever, fatigue, abdominal pain and cramping, weight loss, and anemia in a subject experiencing microbial dysbiosis comprising administering to the subject an effective amount of temocillin, or a pharmaceutically acceptable salt thereof. In one aspect, the microbial dysbiosis of the third embodiment is caused by enterobacterial overgrowth, e.g., AIEC overgrowth.

In a fourth embodiment, provided herein is a method of reducing one or more of inflammation, diarrhea, fever, fatigue, abdominal pain and cramping, weight loss, and anemia in a subject having an intestinal disorder who is also experiencing microbial dysbiosis comprising administering to the subject an effective amount of temocillin, or a pharmaceutically acceptable salt thereof. In one aspect, the microbial dysbiosis of the fourth embodiment is caused by enterobacterial overgrowth, e.g., AIEC overgrowth.

In a fifth embodiment, provided herein is a method of treating an intestinal disorder in a subject experiencing adherent invasive E. coli (AIEC) overgrowth of the intestine, comprising administering to the subject an effective amount of temocillin, or a pharmaceutically acceptable salt thereof. In one aspect, the intestinal disorder of the fifth embodiment is selected from irritable bowel syndrome (IBS) (e.g., diarrhea-associated irritable bowel syndrome (d-IBS), irritable bowel syndrome with constipation (c-IBS), alternating constipating and diarrhea irritable bowel syndrome), Crohn's disease, traveler's diarrhea, colitis, ulcerative colitis, pouchitis, and diverticulitis. In one aspect, the intestinal disorder of the fifth embodiment is Crohn's disease.

In a sixth embodiment, provided herein is a method of modulating (e.g., reducing) adherent invasive E. coli (AIEC) overgrowth in a subject in need thereof, comprising the step of administering to the subject an effective amount of temocillin, or a pharmaceutically acceptable salt thereof. In one aspect, the AIEC overgrowth in the sixth embodiment is in the subject's intestine. In one aspect, the subject of the sixth embodiment has an intestinal disorder. In one aspect, the subject of the sixth embodiment has an intestinal disorder and has AIEC overgrowth of the intestine. In one aspect, the subject of the sixth embodiment has an intestinal disorder selected from irritable bowel syndrome (IBS) (e.g., diarrhea-associated irritable bowel syndrome (d-IBS), irritable bowel syndrome with constipation (c-IBS), alternating constipating and diarrhea irritable bowel syndrome), Crohn's disease, traveler's diarrhea, colitis, ulcerative colitis, and diverticulitis. In one aspect, the subject of the sixth embodiment has an intestinal disorder selected from irritable bowel syndrome (IBS) (e.g., diarrhea-associated irritable bowel syndrome (d-IBS), irritable bowel syndrome with constipation (c-IBS), alternating constipating and diarrhea irritable bowel syndrome), Crohn's disease, traveler's diarrhea, colitis, ulcerative colitis, and diverticulitis and has AIEC overgrowth of the intestine. In one aspect, the subject of the sixth embodiment has Crohn's disease. In one aspect, the subject of the sixth embodiment has Crohn's disease and has AIEC overgrowth of the intestine. In one aspect, the subject of the sixth embodiment has an intestinal disorder selected from irritable bowel syndrome (IBS) (e.g., diarrhea-associated irritable bowel syndrome (d-IBS), irritable bowel syndrome with constipation (c-IBS), alternating constipating and diarrhea irritable bowel syndrome), Crohn's disease, traveler's diarrhea, colitis, ulcerative colitis, pouchitis and diverticulitis. In one aspect, the subject of the sixth embodiment has an intestinal disorder selected from irritable bowel syndrome (IBS) (e.g., diarrhea-associated irritable bowel syndrome (d-IBS), irritable bowel syndrome with constipation (c-IBS), alternating constipating and diarrhea irritable bowel syndrome), Crohn's disease, traveler's diarrhea, colitis, ulcerative colitis, pouchitis and diverticulitis and has AIEC overgrowth of the intestine.

In a seventh embodiment, provided herein is a method of reducing intestinal inflammation caused by adherent invasive E. coli (AIEC) overgrowth in a subject in need thereof (e.g., having Crohn's disease), comprising the step of administering to the subject an effective amount of temocillin, or a pharmaceutically acceptable salt thereof.

In an eighth embodiment, provided herein is a method of reducing one or more of diarrhea, fever, fatigue, abdominal pain and cramping, weight loss, and anemia in a subject having Crohn's disease, comprising orally administering to the subject an effective amount of temocillin, or a pharmaceutically acceptable salt thereof. In one aspect, the subject in the eighth embodiment is experiencing adherent invasive E. coli (AIEC) overgrowth of the intestine.

In a ninth embodiment, a subject of the present methods is administered a pharmaceutically acceptable salt of temocillin.

In a tenth embodiment, the temocillin or pharmaceutically acceptable salt thereof described in the present methods is administered orally.

In an eleventh embodiment, the methods described herein inhibit Enterobacteriaceae overgrowth (e.g., AIEC overgrowth) without inhibiting the growth of bacteria from Firmicutes or Actinobacteria, or both.

In a twelfth embodiment, administration of temocillin reduces the likelihood of recurrence of Enterobacteriaceae overgrowth (e.g., AIEC overgrowth) for a period of at least 7 days post treatment.

The invention can be further understood by reference to the following illustrative examples, which are intended to exemplify non-limiting embodiments of the invention.

EXEMPLIFICATION

General Methods

Temocillin disodium salt was procured from BOC Sciences (45-16 Ramsey Road, Shirley, N.Y. 11967, USA) and from Bellen Chemistry (1 Caida, $3^{rd}$ Street MaoHua Garden, Beijing, China 101300) represented a mixture of 2 diastereomers (R, S) in the ratio of (60, 40). Ciprofloxacin hydrochloride was procured from USP-U.S. (Rockville, MD, USA). Temocillin stocks for all in vivo and in vitro testing was dissolved in 0.9% Sodium Chloride and water was the solvent for Ciprofloxacin was dissolved. Adherent-Invasive E. coli (AIEC) strains were purchased from the Thomas S. Whittam STEC Center (194 Food Safety and Toxicology, Michigan State University, MIC 48824).

Example 1

Activity of Temocillin Against AIECs

The antibacterial activity of temocillin was tested against AIEC and compared with the ciprofloxacin. Briefly, temocillin or ciprofloxacin stocks were diluted in a two-fold series and incubated with the appropriate strain in 96-well sterile polystyrene micro-plates at 35° C. The plates were read by-eye after 16-18 h of incubation to identify the Minimum Inhibitory Concentration (MIC) values. As shown in Table 1, temocillin is effective at 4-8 µg/mL vs. at least 50% of the AIEC Crohn's clinical isolates tested and maintains antibacterial activity vs. ciprofloxacin resistant isolates.

TABLE 1

| Compound | Crohn's AIEC Isolates | | | | | |
|---|---|---|---|---|---|---|
| | #14 | #32 | #40 | #51 | #35 | #49 |
| | MIC, µg/mL | | | | | |
| Temocillin | 16 | 4 | 8 | 8 | 16 | 4 |
| Ciprofloxacin | >8 | >8 | >8 | >8 | >8 | 8 |

Example 2

Decolonization Murine Model Study of Temocillin and Ciprofloxacin

A GI AIEC decolonization murine model studies were performed using a previously published murine model as the basis and run in accordance with animal ethical guidelines at an external contract research organization. Healthy C57BL/6J mice were first administered streptomycin by oral gavage. An AIEC strain (Phylotype D) was then administered at approximately $1-5 \times 10^6$ cfu per mouse by oral gavage and fecal pellets were enumerated for AIEC burden. Upon stable colonization (usually after 48 h post-AIEC administration), mice were sorted into three groups of 4 animals each. One group was given ciprofloxacin while another was given temocillin by oral gavage (both at 30 mg/kg). The third group was the control and was given an equivalent volume of sterile saline by oral gavage. Fecal pellets were recovered at various times as indicated on the X-axis of FIG. 1 and AIEC burden quantified by dilution and plating. Two successive fecal pellets were recovered from each mouse per group to sufficiently power the data.

Temocillin was effective at lowering AIEC burden in the murine GI tract and performed as well as the current standard-of-care antibiotic, ciprofloxacin (FIG. 1). Of particular importance, temocillin was effective at maintaining the AIEC burden low for days after cessation of treatment, whereas ciprofloxacin-treated mice began to show a rebound effect following day 7 after treatment cessation (FIG. 1). This supports the ability of temocillin to reduce the likelihood of recurring AIEC overgrowth post-treatment.

Example 3

Microbiome Sparing Nature of Temocillin

Representatives of human gut anaerobic commensals belonging to the 3 major phyla, Firmicutes, Actinobacteria and Bacteroidetes were tested in standard agar-dilution antibacterial assays run under anaerobic conditions. The work was done externally at a microbiology contract research organization and the results are presented in Table 2. Firmicutes and Actinobacteria are part of the healthy human gut and their levels are compromised in Crohn's patients. As shown, temocillin has little effect (MIC>256 µg/mL) on certain firmicutes, actinobacteria and bacteroidetes.

TABLE 2

| | MIC, µg/mL | | | |
|---|---|---|---|---|
| | Temocillin | Ciprofloxacin | Rifaximin | Metronidazole |
| Firmicutes | | | | |
| MMX 1722 *Lactobacillus casei* | >256 | 1 | 0.25 | >64 |
| MMX 6660 *Streptococcus intermedius* | >256 | 1 | 0.5 | >64 |
| ATCC 23272 *Lactobacillus reuteri* | >256 | 32 | 0.06 | >64 |
| MMX 9797 *Clostridium innocuum* | >256 | 4 | >32 | 1 |
| Actinobacteria | | | | |
| ATCC 15702 *Bifidobacterium infantis* | >256 | 4 | 0.125 | 8 |
| ATCC 25986 *Collinsella aerofaciens* | >256 | 0.5 | ≤0.03 | 1 |
| MMX 10069 *Bifidobacterium adolescentis* | >256 | 32 | 0.5 | 8 |
| Bacteroidetes | | | | |
| ATCC 12290 *Bacteroides thetaiotaomicron* | >256 | 1 | ≤0.03 | 0.25 |
| MMX 9711 *Bacteroides salyersiae* | >256 | 16 | 0.5 | 2 |
| MMX 3478 *Bacteroides fragilis* | 256 | 16 | 0.25 | 8 |
| Proteobacteria | | | | |
| Crohn's Patient #32 AIEC | 4 | >8 | nd | nd |
| Crohn's Patient #40 AIEC | 8 | >8 | nd | nd |
| Crohn's Patient #49 AIEC | 4 | 8 | nd | nd |
| Crohn's Patient #51 AIEC | 8 | >8 | nd | nd |

Example 4

Figure 2A:
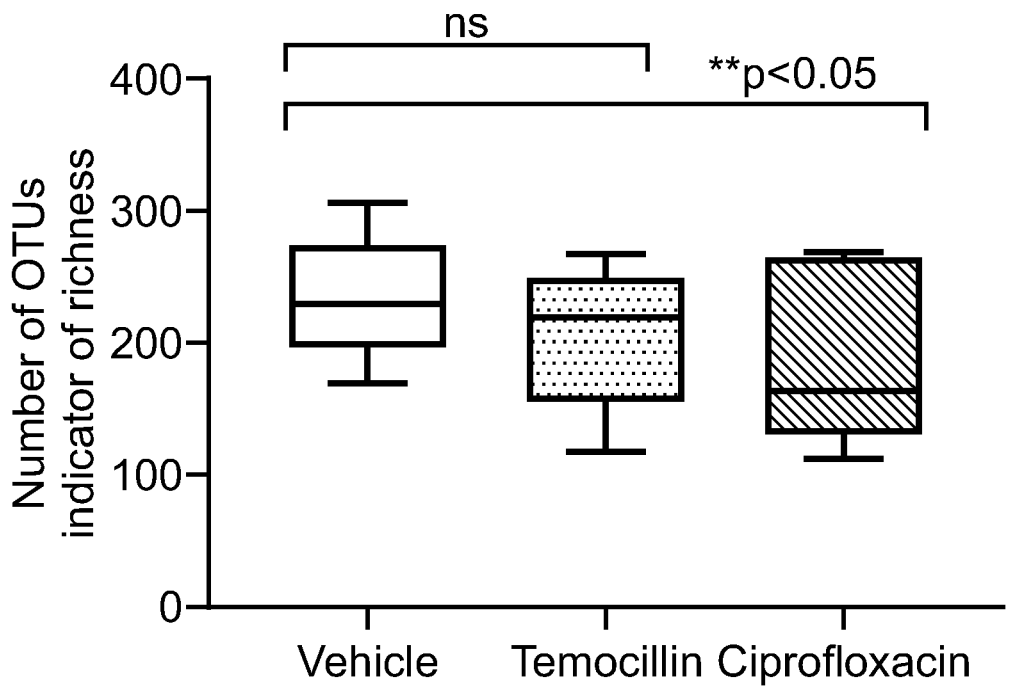
FIG. 2A depicts number of OTUs (indication of richness) obtained from the post-treatment measurement of microbiome health for temocillin and ciprofloxacin in mice.
Figure 2B:
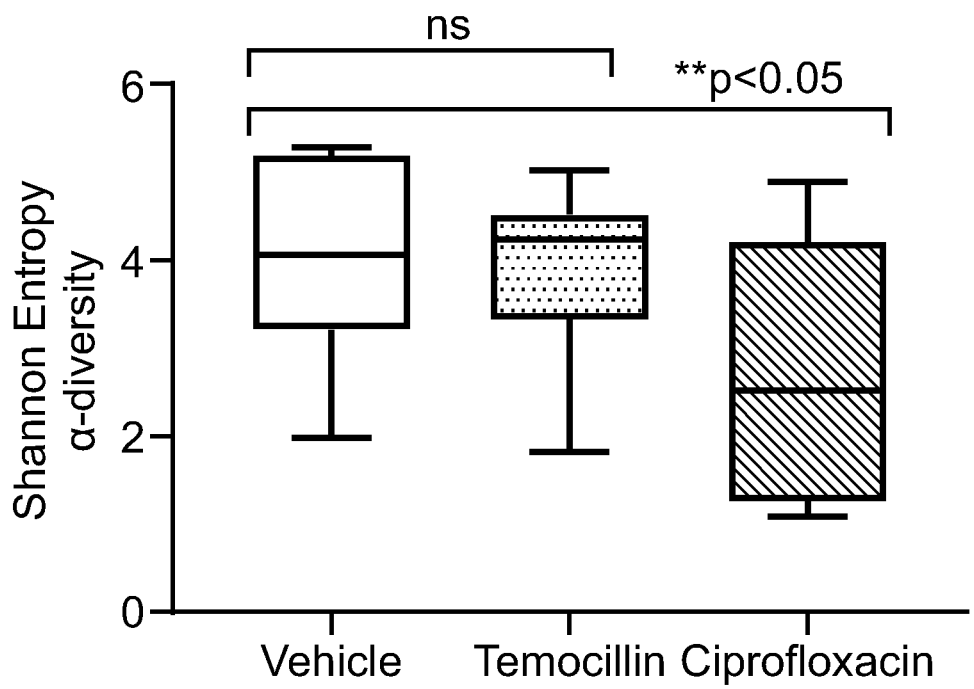
FIG. 2B depicts Shannon entropy index (indication of diversity) obtained from the post-treatment measurement of microbiome health for temocillin and ciprofloxacin in mice.

Post-Treatment Measurement of Microbiome Health for Temocillin and Ciprofloxacin in Mice Mice were treated with 30 mg/kg (by oral gavage) of either temocillin or ciprofloxacin. Mice were dosed once a day for 3 consecutive days post AIEC stable GI colonization. Fecal pellets from four mice (1-2 per mouse) were pooled and subjected to bacterial DNA enrichment and analyzed using the Illumina MiSeq 2. Bacterial abundance and diversity was quantified using 16S rRNA gene sequencing data, analyzed and compared with naïve mice. The richness (FIG. 2A, number of OTUs, $p<0.05$) and diversity (FIG. 2B, Shannon index, $p<0.05$) in mice treated with temocillin were comparable to the untreated (naive) mice and were higher than ciprofloxacin.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A method of treating an intestinal disorder in a subject experiencing adherent invasive *E. coli* (AIEC) overgrowth of the intestine, comprising administering to the subject an effective amount of temocillin, or a pharmaceutically acceptable salt thereof.

2. The method of claim 1, wherein the intestinal disorder is selected from irritable bowel syndrome (IBS) (e.g., diarrhea-associated irritable bowel syndrome (d-IBS), irritable bowel syndrome with constipation (c-IBS), alternating constipating and diarrhea irritable bowel syndrome), Crohn's disease, traveler's diarrhea, colitis, ulcerative colitis, pouchitis, and diverticulitis.

3. The method of claim 1, wherein the intestinal disorder is Crohn's disease.

4. The method of claim 1, wherein the subject is administered a pharmaceutically acceptable salt of temocillin.

5. The method of claim 1, wherein the temocillin or pharmaceutically acceptable salt thereof is administered orally.

6. A method of modulating adherent invasive *E. coli* (AIEC) overgrowth in a subject in need thereof, comprising the step of administering to the subject an effective amount of temocillin, or a pharmaceutically acceptable salt thereof.

7. The method of claim 6, wherein the AIEC overgrowth is in the subject's intestine.

8. The method of claim 6, wherein the subject has an intestinal disorder.

9. The method of claim 6, wherein the subject has an intestinal disorder selected from irritable bowel syndrome (IBS) (e.g., diarrhea-associated irritable bowel syndrome (d-IBS), irritable bowel syndrome with constipation (c-IBS), alternating constipating and diarrhea irritable bowel syndrome), Crohn's disease, traveler's diarrhea, colitis, ulcerative colitis, and diverticulitis.

10. The method of claim 6, wherein the subject has Crohn's disease.

11. The method of claim 6, wherein modulation comprises a reduction in AIEC overgrowth.

12. The method of claim 6, wherein the temocillin or pharmaceutically acceptable salt thereof is administered orally.

13. A method of reducing intestinal inflammation caused by adherent invasive *E. coli* (AIEC) overgrowth in a subject in need thereof, comprising the step of administering to the subject an effective amount of temocillin, or a pharmaceutically acceptable salt thereof.

14. The method of claim 13, wherein the subject has Crohn's disease.

15. A method of reducing one or more of diarrhea, fever, fatigue, abdominal pain and cramping, weight loss, and anemia in a subject having Crohn's disease, comprising orally administering to the subject an effective amount of temocillin, or a pharmaceutically acceptable salt thereof, wherein the subject is experiencing adherent invasive *E. coli* (AIEC) overgrowth of the intestine.

16. The method of claim 13, wherein the temocillin or pharmaceutically acceptable salt thereof is administered orally.

* * * * *